(12) United States Patent
Sheppard et al.

(10) Patent No.: US 6,632,846 B2
(45) Date of Patent: Oct. 14, 2003

(54) INTEGRATED UREA MANUFACTURING PLANTS AND PROCESSES

(75) Inventors: Richard O. Sheppard, Evergreen, CO (US); Dennis L. Yakobson, Arvada, CO (US)

(73) Assignee: Rentech, Inc., Denver, CO (US)

( * ) Notice: Subject to any disclaimer, the term of this patent is extended or adjusted under 35 U.S.C. 154(b) by 0 days.

(21) Appl. No.: 09/963,349

(22) Filed: Sep. 25, 2001

(65) Prior Publication Data

US 2002/0055545 A1 May 9, 2002

Related U.S. Application Data

(63) Continuation-in-part of application No. 09/376,709, filed on Aug. 17, 1999, now Pat. No. 6,306,917.

(51) Int. Cl.[7] .................. C07C 27/00; C07C 273/00; C01C 1/04; F02C 13/10
(52) U.S. Cl. .................. 518/715; 518/700; 518/717; 518/721; 423/359; 564/65; 60/39.02
(58) Field of Search ................. 518/700, 715, 518/717, 721; 423/359; 564/65; 60/39.02

(56) References Cited

U.S. PATENT DOCUMENTS

| | | | |
|---|---|---|---|
| 3,617,498 A | 11/1971 | Kittrell | |
| 3,972,958 A | 8/1976 | Garwood et al. | |
| 3,986,349 A | 10/1976 | Egan | |
| 4,059,648 A | 11/1977 | Derr et al. | |
| 4,092,825 A | 6/1978 | Egan | |
| 4,197,184 A | 4/1980 | Munro et al. | |
| 4,256,654 A | 3/1981 | Schlinger et al. | |
| 4,404,088 A | 9/1983 | Bachtel et al. | |
| 4,433,065 A | * 2/1984 | Van Der Burgt et al. | ... 518/703 |
| 4,496,371 A | 1/1985 | Urban et al. | |
| 4,501,655 A | 2/1985 | Hilfman et al. | |
| 4,549,396 A | 10/1985 | Garwood et al. | |
| 4,579,985 A | 4/1986 | Minderhoud et al. | |
| 4,595,702 A | 6/1986 | Chu et al. | |
| 4,605,639 A | 8/1986 | Dyer et al. | |
| 4,617,288 A | 10/1986 | Bell et al. | |
| 4,902,303 A | 2/1990 | Den Bleyker | |
| 4,957,715 A | 9/1990 | Grover et al. | |
| 4,992,081 A | 2/1991 | Den Bleyker | |
| 4,994,428 A | * 2/1991 | Bell et al. | .............. 502/330 |
| 5,023,276 A | 6/1991 | Yarrington et al. | |
| 5,026,472 A | 6/1991 | Hoehn et al. | |
| 5,324,335 A | 6/1994 | Benham et al. | |
| 5,324,336 A | 6/1994 | Child | |
| 5,403,568 A | 4/1995 | Stowe, Jr. | |
| 5,424,051 A | 6/1995 | Nagji et al. | |

(List continued on next page.)

OTHER PUBLICATIONS

Author: Marcel Dekker, Inc.; Title: The Fischer–Tropsch Synthesis in the Liquid Phase; Date: 1980; Pages :255–275.
Author: Chemical Engineering; Title: Technology to Cool Down Global Warming; Date: 1999; Pages: 37,39,41.

(List continued on next page.)

Primary Examiner—J. Parsa
(74) Attorney, Agent, or Firm—Rick Martin; Patent Law Offices of Rick Martin, PC

(57) ABSTRACT

A plant for manufacturing urea from carbonaceous materials, oxygen from an air separation unit and water, preferably steam, is made up of a syngas generator unit, an air separation unit, Fischer-Tropsch unit, a $CO_2$ removal unit, a hydrogen removal unit, a methanator unit, an ammonia converter unit and a urea synthesizer unit. Each of Fischer-Tropsch liquids, ammonia, hydrogen and urea can be recoverable under proper economic conditions. Electrical power is recoverable by the addition of at least one of a steam turbine and a gas turbine which is/are coupled to an electrical generator.

18 Claims, 5 Drawing Sheets

U.S. PATENT DOCUMENTS

| | | | |
|---|---|---|---|
| 5,500,449 A | | 3/1996 | Benham et al. |
| 5,504,118 A | | 4/1996 | Benham et al. |
| 5,506,272 A | | 4/1996 | Benham et al. |
| 5,543,437 A | | 8/1996 | Benham et al. |
| 5,545,238 A | | 8/1996 | Brooker et al. |
| 5,620,670 A | | 4/1997 | Benham et al. |
| 5,621,155 A | | 4/1997 | Benham et al. |
| 5,645,613 A | | 7/1997 | Benham et al. |
| 5,666,800 A | * | 9/1997 | Sorensen et al. .......... 60/39.02 |
| 5,736,116 A | * | 4/1998 | LeBlan et al. .............. 423/359 |
| 5,763,716 A | | 6/1998 | Benham et al. |
| 6,153,852 A | | 11/2000 | Blutke et al. |
| 6,248,794 B1 | * | 6/2001 | Gieskes ...................... 518/700 |
| 6,306,917 B1 | | 10/2001 | Bohn et al. |

OTHER PUBLICATIONS

Author: Alberto Rivalts; Title: Orimulsion. A new fuel for power generation and future feedstock use; Date: 1996; pp.: 342–344.

Author: Charles B. Benham and Mark S. Bohn; Title: Maximization of Diesel Fuel Production from an Iron–Base Fischer–Tropsch Catalyst; Date: Dec. 1998; pp.: 2–5.

Author: A.R. Jones; Title: The commercial combustion of Orimulsion; Date: 1997; pp.: 318–339.

Author: Mark S. Bohn and Charles B. Benham; Title: A Comparative Study of Alternate Flowsheets Using Orimusion Feedstock; Date: Jan. 1999, pp.: 1–10.

Author: David Gray and Glen Tomlinson; Title: A Novel Configuration for Coproducing Fischer–Tropsch Fuels and Electric Power from Coal and Natural Gas; Date: Sep. 1997; pp.: 1–6.

Author: Dr. Benham and Dennis Yakobson; Title: Optimization of Conversion of Low Hydrogen Containing Feedstocks ?Using Rentech's Gas–To–Liquids (GTL) Technology; Date: Jul. 1998; pp.: 2–19.

Author: Schlesinger, Crowell, Leva, Storch; Title: Fischer–Tropsch Synthesis on Slurry Phase; Date: Jun. 1951; pp.: 1474–1479.

Author: Arthur W. Tower III; Title: Gas–to–Liquids, Solids–yo–Liquids, Liquids–to–Liquids; Date: Dec. 18, 1998; pp.: whole book.

* cited by examiner

INTEGRATED UREA MANUFACTURING PLANTS AND PROCESSES

CROSS REFERENCE TO RELATED APPLICATION

This is a continuation-in-part of U.S. patent application Ser. No. 09/376,709 filed Aug. 17, 1999 now U.S. Pat. No. 6,306,917, titled "Processes for the Production of Hydrocarbons, Power and Carbon Dioxide from Carbon-Containing Materials.

FIELD OF THE INVENTION

Syngas generators such as reformers and gasifiers of hydrocarbon fluids and solid carbonaceous materials and Fischer Tropsch (FT) units for primarily for creating liquid hydrocarbons from syngas are combined to create an integrated plant for providing one or more of urea, ammonia, carbon dioxide, electric power, and even sulfur when dealing with sulfur-containing raw material.

BACKGROUND OF THE INVENTION

Our modern civilization cannot be sustained without burning carbonaceous materials for primarily motive and electrical power within the foreseeable future. The carbon dioxide ($CO_2$) generated by such burning may be contributing to the gradual increase of the planet's temperature since 1900. This is occurring because $CO_2$ permits the sun's energy to pass through the atmosphere but traps the longer wavelength energy radiated by the earth into the atmosphere.

The integrated plants and processes of this invention can help reduce the amount of $CO_2$ currently vented into the air through the production of the various products later discussed in the description of the manufacturing plant flow diagrams. Further, the plants of this invention produce substantial energy savings by balancing exothermic and endothermic reactors as discussed below.

A variety of reformers and gasifiers are known. Thus, U.S. Pat. No. 5,611,947 to J. S. Vavruska, U.S. Pat. No. 5,993,761 to Plotr and Albin Czernichowski et al and U.S. Pat. No. 6,153,852 to A. F. Blutke et al all teach plasma reformers useful in constructing the integrated facilities used in the process of this invention. Likewise, Charles B. Benham et al, U.S. Pat. No. 5,621,155, utilize reformers to provide feed streams to Fischer Tropsch reactors utilizing iron-based catalysts. U.S. patent application Ser. No. 09/376/709, filed Aug. 17, 1999 by Mark S. Bohn et al teaches that hydrocarbons and electric power can be manufactured: at a plant using the Fischer-Tropsch (FT) reactors. It also suggests that urea can be produced but no suggestion is given as to how to manufacture the urea or the practicality of such a course of action.

The mentioned references deal with economic niches where the incentives, regulatory penalties and other incentives must combine with other factors to make the processes commercial. A continuing increase in world temperatures or a more firm tie-in between the $CO_2$ in the atmosphere and increasing world climate temperatures could quickly result in such incentives. The plants can be of particular utility when sited at remote locations where there is a large surplus of natural gas, petroleum, coal or other carbonaceous materials which are presently unrecoverable because of transportation costs, etc.

Increasing regulatory demands have limited, and, in some instances extinguished, the petroleum producers' and refiners' ability to flare waste gases. Further, there are often limitations on the amounts and kinds of other wastes that can be disposed of locally without harm to the environment, e.g., at an offshore crude oil producing platform. The multi-product plants of this invention provide a mechanism for packaging the various unit processes required for the utilization of this invention in a manner that the resulting plants can be utilized to supply electricity for a platform, eliminate the need for flares, convert the waste gases and liquids normally flared into liquid hydrocarbons, ammonia and/or urea while substantially eliminating local $CO_2$ emissions. Solid commercial products can also be produced for agriculture, e.g., sulfur and urea prills. Such self-contained plants provide trade-offs; for offshore petroleum and/or natural gas platforms, which can improve their economic life span. This is particularly true where the deposits being recovered are sour or include some $CO_2$ production.

The unit processes of this invention are each individually well known and are commercially proven. However, the joining of these unit processes as taught herein provides a utility for environmental and other purposes that has heretofore been unforeseen.

SUMMARY OF THE INVENTION

Ammonia, carbon dioxide, hydrocarbons, electric power and urea are producible as products by the reaction of oxygen, water and a carbon source in a syngas generator to produce a syngas, utilizing a water gas shift mechanism to provide $CO_2$, reacting the syngas in an FT reactor to produce FT hydrocarbons and hydrogen, reacting the hydrogen with nitrogen from the air separation oxygen plant to form ammonia, then reacting the $CO_2$ and ammonia to form urea. Electric power can be produced by combustion of hydrogen in a gas turbine used to drive an electricity generator and/or utilizing steam formed during syngas production to drive a steam turbine which, in turn, drives an electricity generator. Sulfur and various heavy metals can be recovered when sulfur or metal-containing carbon sources are utilized. As noted, a number of the compounds, an element and electric power produced in the manufacture of ammonia can be "packaged" for commercial sale.

BRIEF DESCRIPTION OF THE FIGURES

The Figures illustrate the favorable economics and ease of interaction: which can be obtained through a combination of several well known unit processes and for manufacturing a variety of materials, all of which can be provided in amounts suitable for commercial sales if suitable raw materials are available.

DETAILED DESCRIPTION OF THE DRAWINGS

Figure 1:
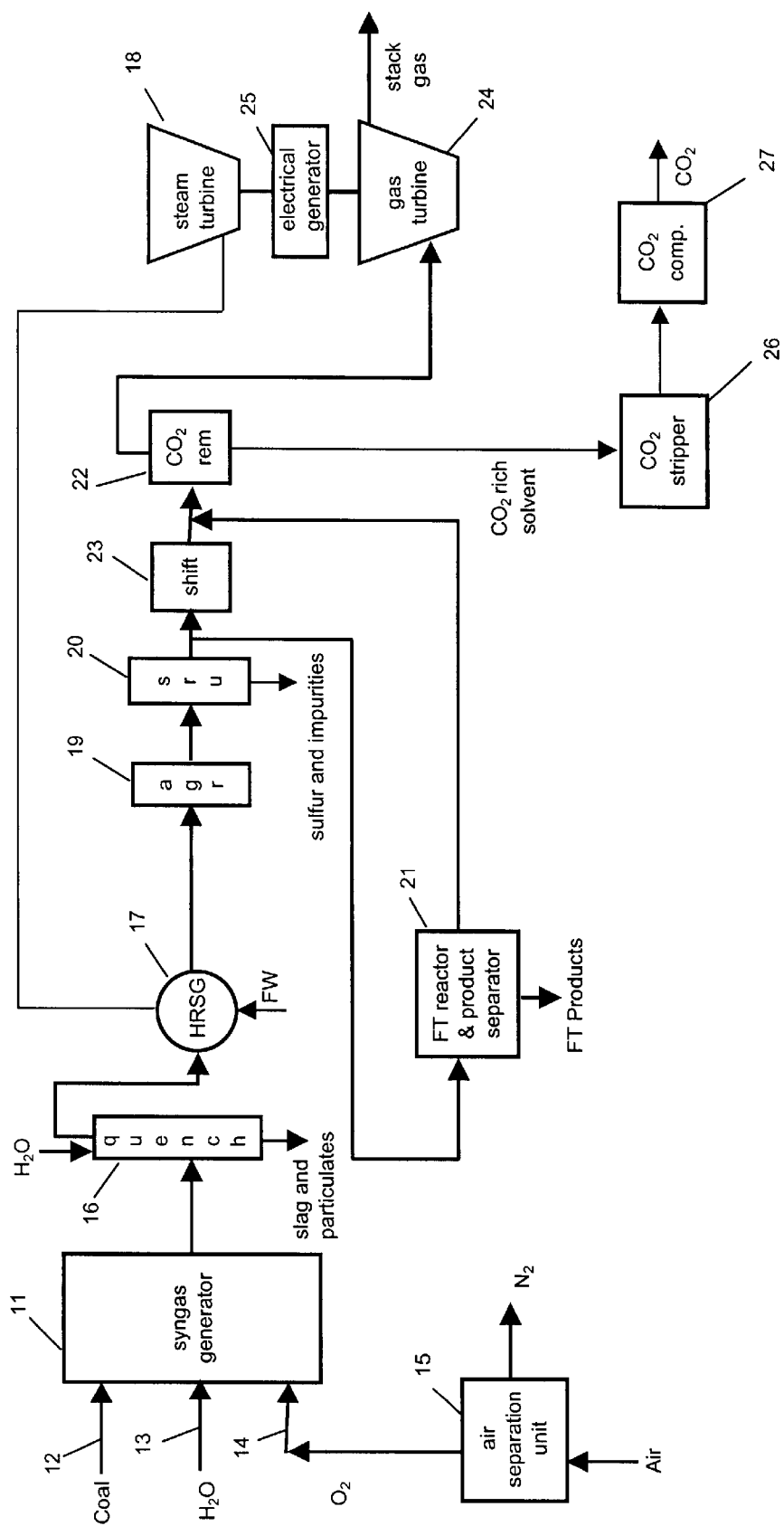
FIG. 1 depicts a syngas producing unit and an FT unit combined to provide liquid hydrocarbons and electric power.

In the coal gasification/FT/power plant of FIG. 1, crushed coal, water ($H_2O$), preferably as steam, and oxygen ($O_2$) are introduced into the syngas generator 11 through piping 12, 13 and 14, respectively. The oxygen is preferably from a cryogenic air separation unit 15. However, pressure swing absorption can also be utilized. Either can provide nitrogen ($N_2$) for an: ammonia (NH3) plant (not shown). The hot gases are exhausted from the syngas generator 11 at temperatures of 2400° F. to 2700° F. and are cooled in one or more water-cooled quench units 16 to remove slag and other minerals. The cooled syngas and soluble impurities are piped into a heat recovery steam generator (HRSG) 17 which is used to heat the feed water (FW) to steam of a desired temperature, e.g., 230° F. to 600° F., and provide steam to power steam turbine 18. The syngas is piped to the acid gas removal unit (AGR) 19 to remove bulk sulfur from the syngas generator 11 output. The resulting gas is then passed through sulfur removal unit (SRU) 20 to remove trace quantities of sulfur. Preferably, the SRU 20 uses a zinc oxide-based catalyst and is run at temperatures of 600° F. to 725° F. with a linear velocity of 4–10 ft/sec.

To the extent needed, the gaseous treated stream from the SRU is then piped to the FT reactor and product separation unit 21 to obtain the liquid FT hydrocarbon products. The FT reactor and product separator 21 tail gas is piped to remove carbon dioxide via $CO_2$ removal unit 22. A second portion of the desulfurized syngas is piped to a water gas shift reactor 23, preferably designed for use with a high temperature iron/chrome catalyst. The tail gas stream from the FT reactor and product separation unit 21 is combined with the output of the shift reactor 23 and passed through $CO_2$ removal unit(s) 22. Combustible components from the $CO_2$ removal unit(s) 22 are fed to the gas turbine 24 which is used to drive a coupled electricity generator 25. Likewise, the steam turbine 18 can be used to drive the electrical generator (s) 25. The stack gases of the gas turbine 24 are returned to heat recovery steam generator (HRSG) 17.

The $CO_2$ absorbed in the $CO_2$ removal unit 22 is desorbed in the $CO_2$ stripper unit 26 and compressed by $CO_2$ compressor(s) 27 for tank or other storage, preferably at pressures above 135 atm or recycled as needed.

Figure 2A:
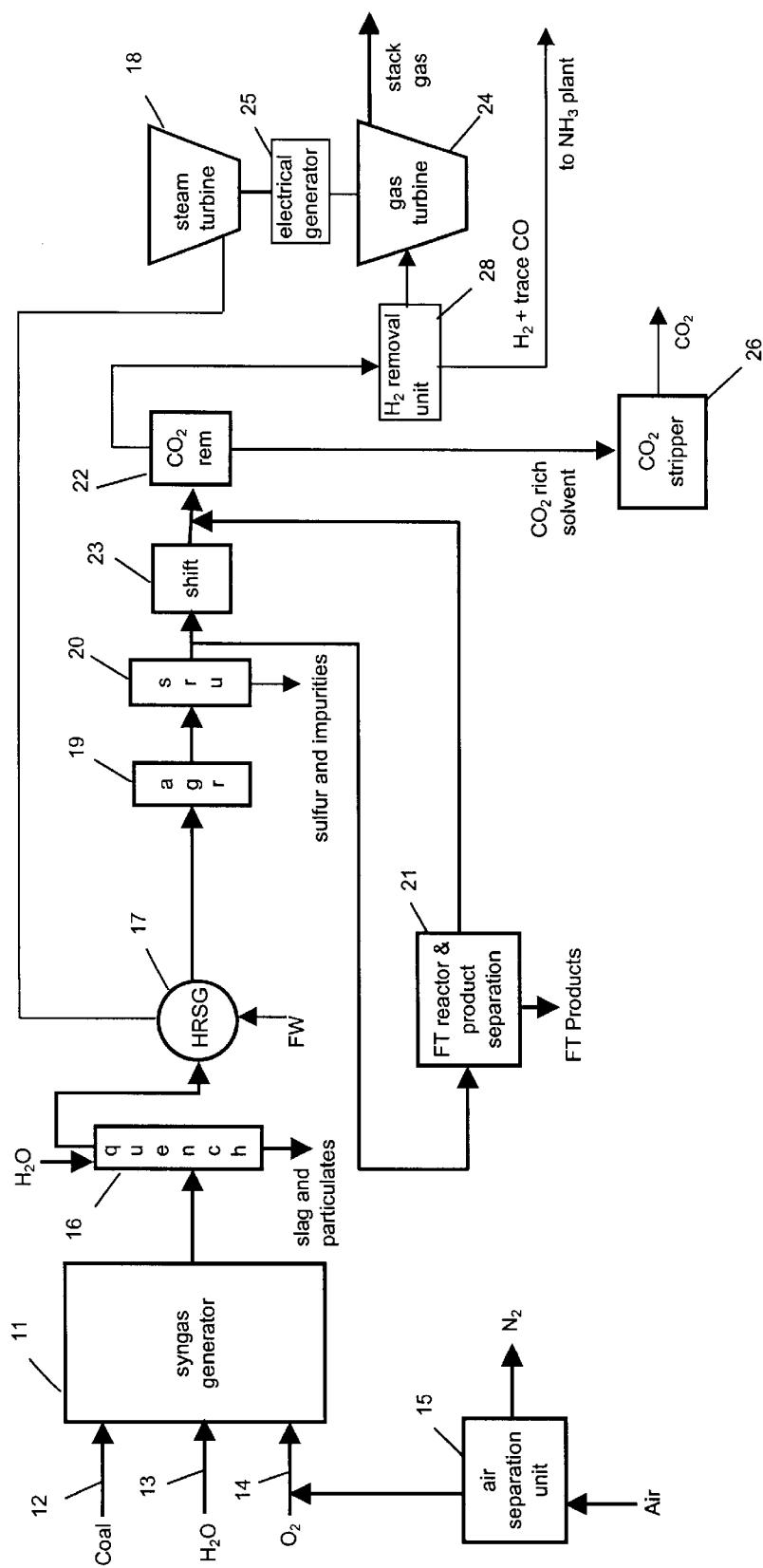
FIG. 2a utilizes the basic plan of FIG. 1 and delineates the minimal equipment and indicates the valving and other plumbing changes needed to convert the unit of FIG. 1 into an ammonia manufacturing plant utilizing hydrocarbon gases from a substantially solid carbonaceous feed such as coal and petroleum refining residues.
Figure 2B:
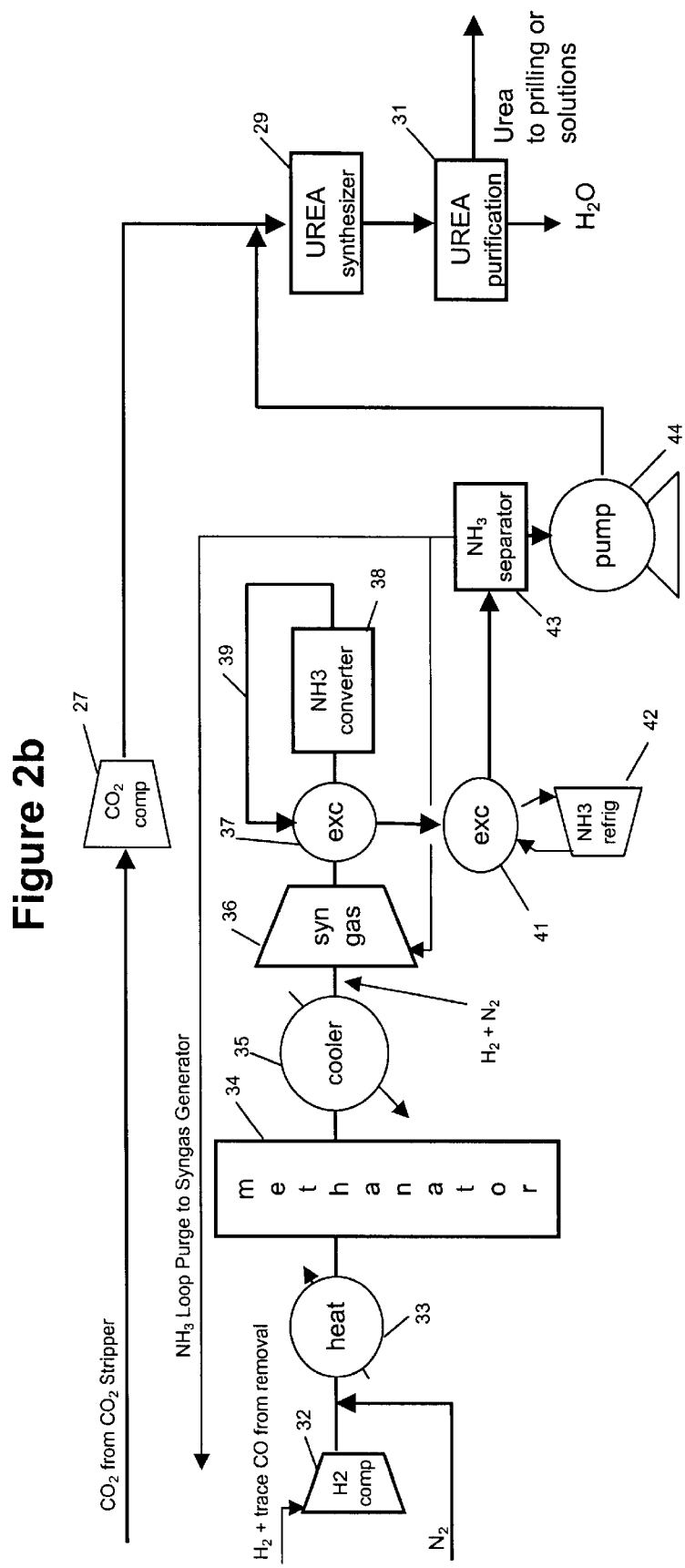
FIG. 2b depicts the added equipment needed to convert the ammonia produced in the plant of FIG. 2a into a urea plant.

In FIG. 2a, the equipment differs from that of FIG. 1 only to the extent that the non-$CO_2$ output of the $CO_2$ removal unit 22 is passed through a hydrogen ($H_2$) removal unit 28 and the recovered hydrogen is piped to an ammonia converter 38 (FIG. 2b). The hydrogen contains trace amounts of carbon monoxide which fuel the smaller methanator 34 (FIG. 3b). The non-$H_2$ output of the $H_2$ removal unit (HRU) 28 is piped to the gas turbine 24 as fuel. Preferably the $H_2$ removal unit 28 utilizes a membrane separator. Such units are manufactured by Monsanto Company, located at St. Louis, MO., USA or Air Liquide located at Paris, France.

In FIG. 2b, the continuation of the flow chart of FIG. 2a, the $CO_2$ from stripper unit 26 (FIG. 2a) is compressed by $CO_2$ compressor 27 and introduced into urea synthesizer 29 which operates at 330° F. to 375° F. and 2000 to 3000 psig. The urea synthesized in the urea synthesizer 29 is pumped to the urea purification unit 31 to reduce the water and other impurities. The urea is then prilled or formulated into aqueous urea or anhydrous prills for sale.

Hydrogen ($H_2$) from the hydrogen removal unit 28 (FIG. 2a) is passed through hydrogen compressor 32 and combined with nitrogen ($N_2$) from air separation unit 15 and the mixture is passed to heater 33 to raise the temperature to about 500° F. and introduced into methanator 34 to remove carbon oxides. The methanator 34 operates at 500° F. to 600° F. utilizing, preferably, a 27–35% nickel oxide catalyst.

The methanator utilizes a catalyst which is delivered as nickel oxide on alumina and reduced to nickel on site for operation. A variety of suppliers market the catalyst. The methanator operates at temperatures between about 500° F. to 550° F. at the inlet and pressures between about 275 to about 375 psig. The methanator 34 product stream is passed through cooler 35 into ammonia/syngas compressor 36. The compressed product stream is cooled in exchanger 37 and is fed to $NH_3$ converter 38. The resulting ammonia stream returns to the heat exchanger 37 through line 39. The cooled effluent is further cooled in exchanger 41 and still further cooled with a cold stream from ammonia refrigeration unit 42 before passing to separator 43. The condensed ammonia from, ammonia separator 43 is then passed through pump 44, piped into a urea synthesizer 29, dried for prilling or made into aqueous solutions of desired concentrations.

Figure 3A:
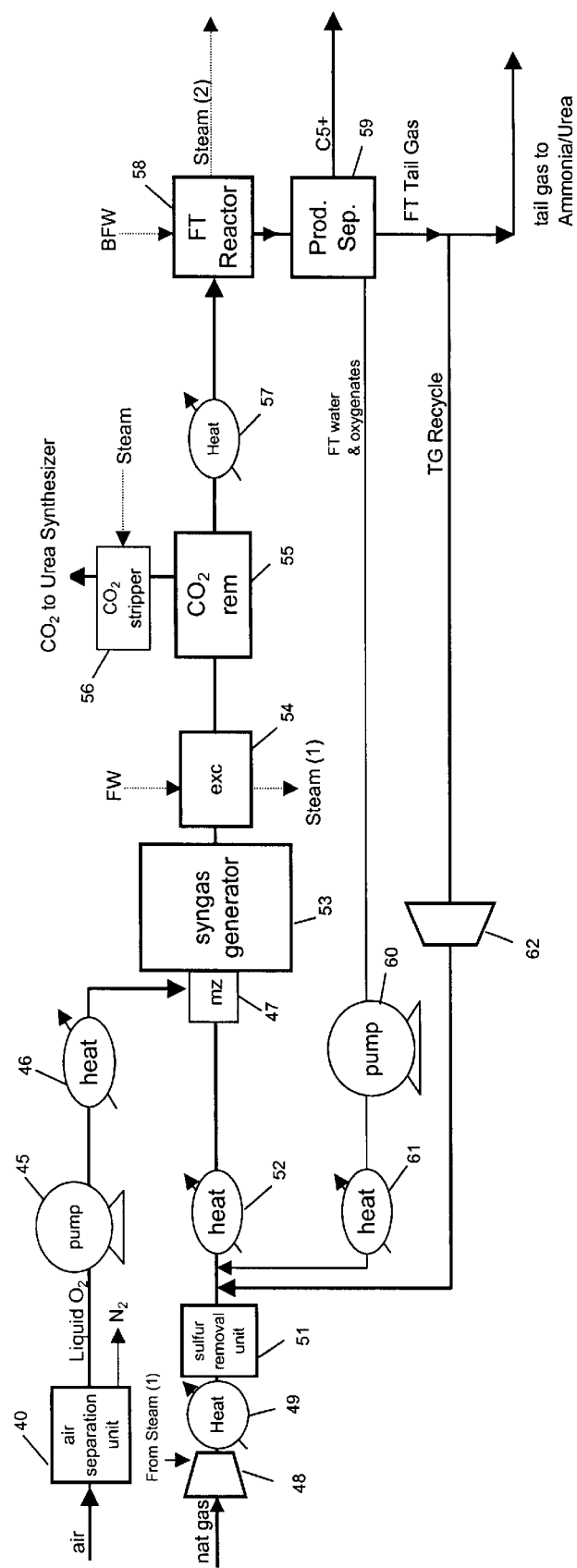
FIGS. 3a and 3b teach an alternate exemplary plant layout for manufacturing urea utilizing natural gas as the syngas feedstock.
Figure 3B:
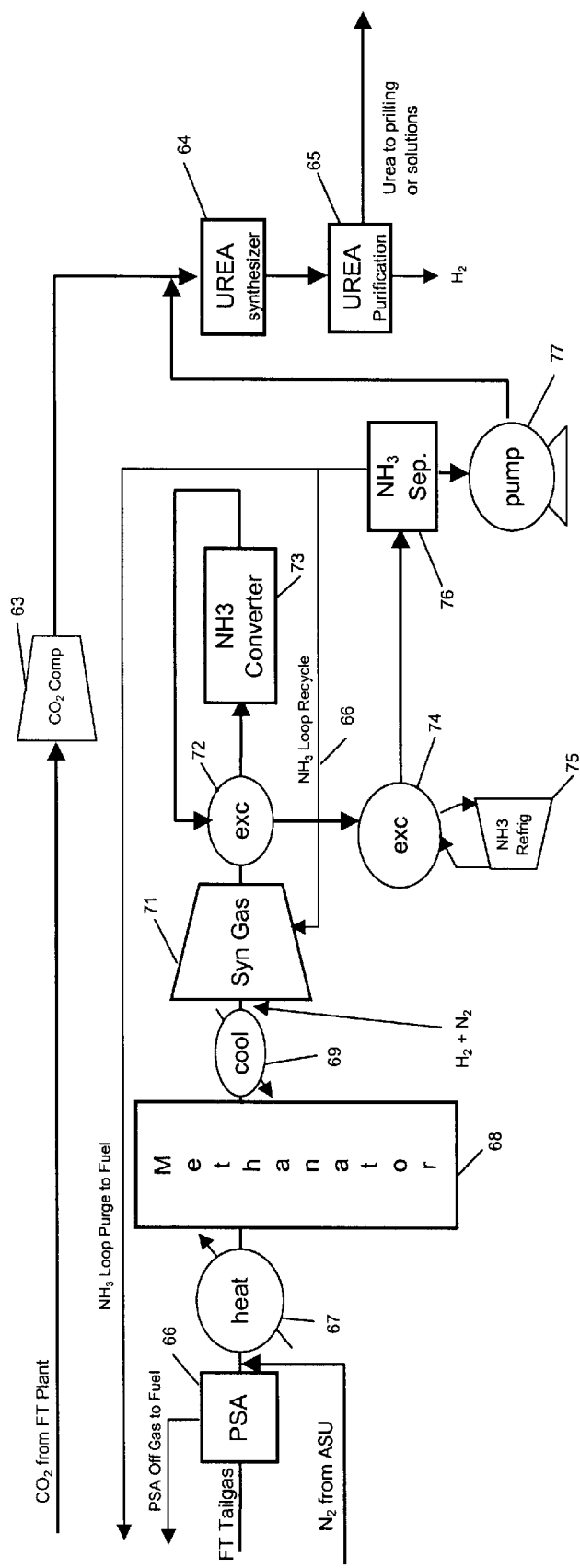

In FIG. 3a, the liquid oxygen ($O_2$) from air separation unit 40 is passed through cryogenic pump 45, heater 46 and introduced into mixing zone 47. The natural gas is compressed to about 200 to about 500 psia in compressor 48, heated in exchanger 49 and run through a sulfur removal unit 51 to "sweeten" the raw gas and then into another heater 52 before entering the mixing zone 47. The natural gas and oxygen are converted into syngas in syngas generator 53 and cooled in exchanger 54 prior to treatment in $CO_2$ removal unit 55.

The absorbed $CO_2$ is stripped in stripper 56 prior to recycling to the urea synthesizer 29 (FIG. 3b). The syngas stream passes through heater 57 before entering FT reactor 58. The resulting products are introduced into product separator 59 to provide a liquid hydrocarbon stream with pentane or greater fractions, a stream of aqueous oxygenated hydrocarbons which is pumped from about 200 to about 500 psia by pump 60, and reheated in heat exchangers 61 and 52 prior to entering mixing zone 47. A tail gas stream also flows to mixing zone 47 via compressor 62 while the $CO_2$ is sent to a $CO_2$ compressor 63 (FIG. 3b). The flow diagram of FIG. 3b shows $CO_2$ from the $CO_2$ stripper 56 passing through compressor 63 into urea synthesizer 64 and thence through a urea purification unit 65. The FT tail gas stream then passes a pressure swing absorber 66 to remove $H_2$. A hydrogen-lean fraction is used as fuel while the remainder is mixed with nitrogen ($N_2$) from air separation unit 40, piped to heater 67 and thence to methanator 68 which removes the remaining traces of carbon oxides. The product stream from the methanator is piped into cooler 69 and then into ammonia syngas compressor 71. The compressor 71 product is cooled in exchanger 72 and introduced into ammonia converter 73. The ammonia from the converter 73 is fed to the exchanger 72, cooled in exchanger 74 by ammonia refrigeration unit 75. The ammonia stream from exchanger 74 passe s through ammonia separator 76. A portion of the effluent from separator 76 is recycled to the ammonia syngas compressor 71 and the remainder is used as fuel. The purified ammonia is passed through pump 77 and mixed with compressed $CO_2$ before introduction to urea synthesizer 64. The urea produced is then passed through purifier 65 and readied for use or sale.

EXAMPLES

Example 1

Coal Gasification to FT Liquids, Electrical Power and $CO_2$

Example 1 is a computer simulation based on the flow sheet of FIG. 1. 5500 tpd Pittsburgh #8 coal is gasified with 3328 tpd water and 5156 tpd oxygen. The coal is 74.16% carbon. After quenching and cleaning, a portion of the syngas is sent to an FT reactor. The remainder of the syngas is shifted to convert as much of the CO to $CO_2$ as is possible. This shifted stream is combined with the FT reactor tail gas. $CO_2$ is removed from the combined stream and compressed for commercial usage or sequestration. The $CO_2$-free gas is sent to the gas turbine to produce power.

The flow sheet takes advantage of the water-gas shift activity of an iron-based FT catalyst in converting much of the carbon in the feed coal to $CO_2$. This catalyst is discussed in U.S. Pat. No. 5,504,118 issued to Charles B. Benham et al. A computer simulation utilizing the equipment of this flow sheet of 5500 ton per day of coal produces 6000 barrels per day of FT liquids, 400 MW net electrical power, and 10515 ton per day of sequesterable $CO_2$. Only 9% of the feed carbon is in the stack gas.

Example 2

Coal Gasification to FT Liquids, Electrical Power and Urea

Example 2 is based on the flow sheet of FIGS. 2a and 2b. This flow sheet builds on the flow sheet of Example 1 by reacting the sequestered $CO_2$ with ammonia to produce urea. To make the required ammonia, nitrogen from the air separation unit is reacted with hydrogen removed from the gas stream prior to power generation. This demonstrates the synergies possible with the iron-based FT catalyst.

Using these two flow sheets, a computer simulation based on 5500 ton per day coal produces 6000 barrels per day FT liquids, 223 MW net electrical power and 4230 ton per day urea. Carbon in the stack gas is the same as in Example 1. The difference is that the sequestered $CO_2$ has been used to produce urea.

Example 3

Natural Gas to FT Liquids and Urea

This example is based on FIGS. 3a and 3b and the use of a sour natural gas. The natural gas is reformed with oxygen in an autothermal reformer. After cooling the syngas, $CO_2$ is removed and sent to the urea plant. The syngas is then sent to an FT reactor. Most of the FT tail gas is recycled to the autothermal reactor. The rest is used in the ammonia plant. Ammonia and $CO_2$ are removed from the syngas and piped to the urea plant.

In this flow sheet, a computer simulation shows that 100 MMSCFD natural gas produces 10,170 barrels per day FT liquids and 275 ton per day urea. Note that virtually all of the feed carbon ends up in the FT liquids and the urea.

Simulation of the coal gasifier was based on synthesis gas composition given in Table 1 of "Syngas Production from Various Carbonaceous feedstocks", Texaco Gasification Process for Solid Feedstocks, Texaco Development Corporation, 1993. Simulation of the Fischer-Tropsch reactor was based on Rentech's iron-based catalyst (U.S. Pat. No. 5,504,118).

GENERAL TEACHING OF THE INVENTION

The obvious benefits of utilizing the unit operations and processes of this invention include:

With respect to FIGS. 1, 2a and 2b, there is an unexpected benefit from shifting the use of the coal gasifier operation to convert the usually, desired CO to $CO_2$ production. It enables the heat values of the syngas to simultaneously produce electrical power and sequester $CO_2$. The use of iron-based FT catalysts to form $CO_2$ from CO allows some of the feed carbon to be sequestered as $CO_2$. When the sequestered $CO_2$ is reacted with hydrogen recovered from the syngas production, the FT tail gas and nitrogen from the air separation unit, a synergistic benefit is obtained via the production of urea. Further, when $CO_2$ from a reformed natural gas feed, $H_2$ obtained from the FT tail gas and the nitrogen obtained from the air separation unit are reacted as shown, urea can be produced rather than having to vent the $CO_2$ to the atmosphere.

Feedstocks include both natural gas and low value industrial materials, e.g., coal and refinery bottoms having a hydrogen to carbon atom ratio of about 1. Feedstocks can, however, have higher ratios, e.g., natural gas with a ratio approaching 4:1. Many of these materials will include contaminants which must be removed, e.g., sulfur, arsenic and silicaceous materials which are removed during the course of the syngas manufacturing steps as slag or sulfur compounds.

The syngas produced can be contaminated with carbon dioxide and unwanted impurities such as chlorine, chlorides and other toxic materials which must be safely removed and stored.

For the purposes of this invention, iron-based FT catalysts are preferred because they produce $CO_2$ and $H_2$ via their water gas shift activity. In general, the reactors, materials of construction and processes are well known to those skilled in the refining and Fischer Tropsch utilizing industries. The assembly of the reactors taught form the basis of the claimed chemical processing units sequenced in the invention. The sequenced chemical processes, catalysts, temperatures, concentrations and other stated parameters form the basis of the chemical process claims. It is to be understood that the order of the chemical processing units and the process steps and conditions described in Figures and the discussion thereof can be varied and the variations are intended to fall within the claims as taught in the description and Figures.

We claim:

1. The process comprising separating oxygen from nitrogen from the air in an air separation unit, introducing a carbonaceous raw material, water and oxygen from the air separation unit into a syngas generator under syngas forming operating conditions, utilizing a shift reaction to form substantially syngas and carbon dioxide; introducing the syngas into a Fischer-Tropsch reactor and forming aliphatic hydrocarbons utilizing an iron-based Fischer-Tropsch reactor catalyst; separating the aliphatic hydrocarbons, carbon dioxide, carbon monoxide, and hydrogen; introducing nitrogen from the air separation unit and the syngas and hydrogen, into a methanator to form methane and then into an ammonia converter to produce ammonia; separating the ammonia; introducing the $CO_2$ and ammonia formed into a urea synthesizer under urea-forming conditions and recovering the urea.

2. The process of claim 1 wherein the feedstock to the syngas generator and reactant composition are adjusted to produce syngas and the Fischer-Tropsch reactor catalyst is a precipitated iron catalyst promoted with copper and potassium.

3. The process of claim 1 wherein at least a portion of the hydrogen produced by the syngas generator is burned in the gas turbine of a combined cycle plant to drive a generator mechanically coupled to the gas turbine during the production of electricity.

4. The process of claim 1 wherein at least a portion of the steam recovered from the syngas generator and Fischer-Tropsch unit operations is introduced into the steam turbine of a combined cycle plant to drive a generator mechanically coupled to the steam turbine during the production of electricity.

5. The process of claim 1 wherein at least a portion of the ammonia from the ammonia converter is separated and compressed and packaged for commercial sale.

6. The process of claim 1 wherein the sulfur from the sulfur removal unit is packaged for commercial sale.

7. The process of claim 1 wherein at least a portion of the hydrogen from the Fischer-Tropsch reactor is recovered and packaged for commercial sale.

8. The process of claim 1 wherein at least a portion of the carbon dioxide is recovered from the carbon dioxide stripper and packaged for commercial sale.

9. A process for manufacturing primarily aliphatic hydrocarbons and urea from carbonaceous materials comprising:
   a) reacting a carbonaceous material with steam and oxygen from an air separation unit in a syngas generator to produce a mixture of gases containing hydrogen, carbon monoxide and carbon dioxide;
   b) reacting the mixture of gases in a Fischer-Tropsch reactor unit containing at least one iron-based catalyst for the formation of aliphatic hydrocarbons and for the formation of carbon dioxide via the water gas shift reaction;
   c) separating the aliphatic hydrocarbons from the Fischer-Tropsch product gases;
   d) separating carbon dioxide from the product gases;
   e) separating hydrogen from the product gases;
   f) reacting the separated hydrogen and nitrogen from the air separation unit with the residual Fischer-Tropsch gases in a methanator unit to form methane;
   g) reacting the methanator off gases in an ammonia converter;
   h) separating ammonia from the ammonia converter off gases; and
   i) reacting separated carbon dioxide with the separated ammonia in a urea synthesizer and recovering urea.

10. The process of claim 9 wherein the Fischer-Tropsch reactor includes an iron-based catalyst and the syngas generator operates at about 2400° F. to about 2700° F.

11. The process of claim 9 wherein the catalyst used in the Fischer-Tropsch catalyst is a precipitated unsupported iron catalyst.

12. The process of claim 10 wherein the catalyst is promoted with potassium and copper.

13. The process of claim 9 wherein carbonaceous material contains sulfur and the sulfur is removed from the natural gas prior to reaction in the syngas generator.

14. The process comprising separating oxygen from nitrogen from the air in an air separation unit, introducing a carbonaceous raw material, water and oxygen from the air separation unit into a syngas generator under syngas forming operating conditions, introducing a portion of the syngas into a Fischer Tropsch reactor containing an iron-based catalyst and forming primarily aliphatic hydrocarbons and carbon dioxide; separating the liquid hydrocarbons from the carbon dioxide and unconverted carbon monoxide and hydrogen in the Fischer Tropsch tail gases; introducing a portion of the syngas along with water and the Fischer Tropsch tail gases into a water-gas-shift reactor to product primarily hydrogen and carbon dioxide; scrubbing the carbon dioxide from the shift reactor effluent and collecting it for sale or sequestration; burning the gases rich in hydrogen from the $CO_2$ scrubber in a gas turbine combustor of a combined cycle plant to drive a generator mechanically coupled to the gas turbine during the production of electricity.

15. The process of 14 wherein the catalyst used in the Fischer Tropsch reactor is unsupported precipitated iron.

16. The process of claim 15 wherein the Fischer Tropsch catalyst is promoted with potassium and copper.

17. The process of claim 15 wherein the weight ratio of potassium to iron in the catalyst is between 0.007 and 0.010.

18. The process of claim 15 wherein the weight ratio of copper to iron in the catalyst is between 0.005 and 0.015.

\* \* \* \* \*

UNITED STATES PATENT AND TRADEMARK OFFICE
CERTIFICATE OF CORRECTION

PATENT NO.     : 6,632,846 B2
DATED          : October 14, 2003
INVENTOR(S)    : Richard O. Sheppard and Dennis L. Yakobson It is certified that error appears in the above-identified patent and that said Letters Patent is hereby corrected as shown below:

Title page,
Item [63], Related U.S. Application Data, delete.

Column 1,
Lines 4-5, delete "CROSS REFERENCE TO RELATED APPLICATION"; and
Lines 6-10, delete "This is a continuation-in-part of U.S. patent application Ser. No. 09/376,709 filed Aug. 17, 1999 now U.S. Pat. No. 6,306,917, titled "Processes for the Production of Hydrocarbons, Power and Carbon Dioxide from Carbon-Containing Materials.".

Signed and Sealed this

Sixteenth Day of May, 2006

JON W. DUDAS
*Director of the United States Patent and Trademark Office*